United States Patent [19]

Rooney et al.

[11] 4,105,769

[45] Aug. 8, 1978

[54] INHIBITION OF INDOLEAMINE-N-METHYL TRANSFERASE BY 2-IMINOPYRIDINES

[75] Inventors: Clarence S. Rooney, Beaconsfield; Joshua Rokach, Laval, both of Canada; Edward J. Cragoe, Jr., Lansdale, Pa.

[73] Assignee: Merck & Co., Inc., Rahway, N.J.

[21] Appl. No.: 761,748

[22] Filed: Jan. 24, 1977

[51] Int. Cl.² .................... A61K 31/44; C07D 211/72
[52] U.S. Cl. ............................... 424/263; 260/296 R; 260/297 Z; 260/326.85
[58] Field of Search .................... 260/296 R; 424/263

[56] References Cited

U.S. PATENT DOCUMENTS 2,810,726 10/1957 Howard ..................... 260/296 R

OTHER PUBLICATIONS

Foye, W. O., et al., J. Pharm. Sci., 57(2), 345–348 (1968).
Curphey, T. J., Organic Syntheses, R. E. Benson, ed., vol. 51, John Wiley and Sons, New York, 1971, pp. 144–146.
Vogel, E., et al., Justus Liebigs Ann. Chem., 682, 11 (1965).

*Primary Examiner*—Henry R. Jiles
*Assistant Examiner*—Richard A. Schwartz
*Attorney, Agent, or Firm*—William H. Nicholson; Harry E. Westlake, Jr.

[57] ABSTRACT

A method of inhibiting indoleamine-N-methyl transferase comprises the administration to a host of a therapeutically effective amount of 1-alkyl-2-iminopyrrolidines or 1-alkyl-2-iminopyridines or pharmaceutically acceptable salts thereof.

4 Claims, No Drawings

INHIBITION OF INDOLEAMINE-N-METHYL TRANSFERASE BY 2-IMINOPYRIDINES

The present invention relates to novel and useful pharmaceutical compositions and a method of treatment. More specifically, it relates to compositions and a method for inhibiting indoleamine-N-methyl transferase by the administration of 1-alkyl-2-iminopyrrolidines or 1-alkyl-2-iminopyridines or pharmaceutically acceptable salts thereof.

N,N-dimethylindoleamines are generally psychotomimetic agents and some of these (e.g. dimethylserotonin and dimethyltryptamine) may be produced in excessive amounts by patients with mental aberrations (i.e. schizophrenia). Indoleamine-N-methyl transferase catalyzes the methylation steps in the biosynthesis of these compounds. Accordingly, inhibitors of this enzyme are of therapeutic value in the management of the body chemistry of patients having mental aberrations and in alleviating some symptoms of the disease.

It is an object of the present invention to provide compositions which inhibit indoleamine-N-methyl transferase. Another object is to provide a method of inhibiting the transferase with the active compounds and novel compositions thereof.

The compounds employed in the novel method of treatment have the following structural formula:

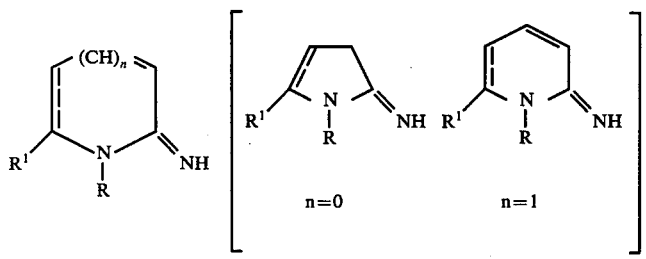

or a pharmaceutically acceptable salt thereof, wherein
n is 0 or 1;
R is lower alkyl, especially $C_{1-3}$ alkyl;
$R^1$ is hydrogen or amino; and the dotted line represents saturation or unsaturation.

Some of the compounds useful in the composition and method of treatment of this invention are known in the art, available commercially or may be prepared by well known prior art methods. For example, 1-alkyl-2-iminopyrrolidines are described in J. Org. Chem., 32, 738 (1967), and 1-alkyl-1H-2-iminodihydropyridine is described in Chem. Ber., 54 B, 814 (1921). The compound, 2-imino-1-methyl-1,2,5,6-tetrahydropyridine, is a new compound and forms another embodiment of this invention.

The pharmaceutically acceptable salts coming within the purview of this invention are acid-addition salts prepared from other acid addition salts or the free bases by standard procedures. Acids useful for preparing these salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, succinic, p-aminobenzoic, p-acetamidobenzoic, methanesulfonic, ethanedisulfonic, or isethionic acid.

In general, the daily dose can be from about 0.10 mg./kg. to about 100 mg./kg. per day and preferably from 1 mg./kg. to 10 mg./kg. per day, bearing in mind, of course, that in selecting the appropriate dosage in any specific case, consideration must be given to the patient's weight, general health, metabolism, age and other factors which influence response to the drug.

Another embodiment of this invention is the provision of pharmaceutical compositions in unit dosage form which comprise from about 5 mg. to 500 mg. of a compound of the above formula.

The pharmaceutical compositions may be in a form suitable for oral use, for example, as tablets, solutions, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, for example calcium carbonate, sodium carbonate, lactose, calcium phosphate or sodium phosphate; granulating and disintegrating agents, for example, maize starch or alginic acid; binding agents, for example, starch, gelatin or acacia, and lubricating agents, for example, magnesium stearate, stearic acid or talc. The tablets may be uncoated or they may be coated by known techniques to delay disintegration and adsorption in the gastro-intestinal tract and thereby provide a sustained action over a longer period.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is dissolved or mixed with an oil or aqueous medium, for example, arachis oil, liquid paraffin, olive oil or water.

Aqueous suspensions or solution containing the active compound in admixture with excipients are suitable for the manufacture of aqueous suspensions. Such excipients are suspending agents, for example, sodium carboxymethyl cellulose, methylcellulose, hydroxypropylmethylcellulose, sodium alginate, polyvinylpyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products or ethylene oxide with long chain aliphatic alcohols, for example heptadecaethyleneoxy-cetanol, or condensation products of ethylene oxide with partial esters derived from fatty acids and a hexitol, for example polyoxyethylene sorbitol mono-oleate, or condensation products of ethylene oxide with partial esters derived from fatty acids and hexitol anhydrides, for example polyoxyethylene sorbitan mono-oleate. The said aqueous suspensions may also contain one or more preservatives, for example ethyl, or n-propyl p-hydroxybenzoate, one or more coloring agents, one or more flavoring agents and one or more sweetening agents, such as sucrose, saccharin, or sodium or calcium cyclamate.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally occurring gums, for example gum acacia or gum tragacanth, naturally occurring phosphatides, for example soya bean lecithin, and esters of partial esters derived from fatty acids and hexitol anhydrides, for example sorbitan mono-oleate and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous solution or suspension. This aqueous medium may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1:3 butane diol.

The pharmaceutical compositions may be tableted or otherwise formulated so that for every 100 parts by weight of the composition there are present between 5 and 95 parts by weight of the active ingredient and preferably between 25 and 85 parts by weight of the active ingredient. The dosage unit form will generally contain between about 0.10 mg. and about 500 mg. of the active ingredient of the formulae stated above.

From the foregoing formulation discussion it is apparent that the compositions of this invention can be administered orally or parenterally. The term parenteral as used herein includes subcutaneous injection, intraveneous, intramuscular, or intrasternal injection or infusion techniques. In addition, the compounds can be given rectally as suppositories or topically with penetrants.

The following examples are presented to further illustrate the invention.

EXAMPLE 1

1-Ethyl-2-iminopyrrolidine

2-Amino-1-pyrroline (1.26 g., 15 mmoles) and 4.68 g. (30 mmoles) of ethyl iodide were refluxed in 10 ml. of ethanol for 2 hours. The cooled mixture was diluted with ether and refrigerated overnight. The oil that precipitated was collected, dissolved in methanol and treated with excess potassium carbonate. The solvent was evaporated and the residue was extracted with chloroform, and the chloroform was concentrated to dryness. This residue was dissolved in alcohol and treated with 1 g. of oxalic acid. After heating to provide a clear solution, it was cooled and treated with ether to incipient cloudiness. The solid that separated was discarded, and the mother liquors were concentrated to dryness. The residue was dissolved in water and extracted with chloroform. The aqueous solution was basified with sodium hydroxide solution, and extracted with chloroform. Concentration of the chloroform to dryness provided 630 mg. of oily 1-ethyl-2-iminopyrrolidine which was converted to 680 mg. of the hydrogen oxalate salt, m.p. 68°–75° C. (as a hydrate).

EXAMPLE 2

2-Imino-1-methyl-1,2,5,6-tetrahydropyridine

Step A: Preparation of 1-methyl-2-oxo-1,2,5,6-tetrahydropyridine

A mixture of 20 g. of vinylacrylic acid, 400 ml. of methylamine solution (40% aqueous by weight) and 0.5 g. of hydroquinone was heated overnight at 170° C. in a stainless steel pressure vessel. After cooling, the mixture was concentrated to dryness and the residue was fractionally distilled. The fraction distillng at 125°–130° C. at 0.4–0.5 mm. Hg. (12.5 g.) was shown by n.m.r. to be the desired 1-methyl-2-oxo-1,2,5,6-tetrahydropyridine.

Steps B: Preparation of 2-imino-1-methyl-1,2,5,6-tetrahydropyridine

A mixture of 3.0 g. of 1-methyl-2-oxo-1,2,5,6-tetrahydropyridine from Step A, 50 ml. of methylene chloride, and 4.1 g. of trimethyl oxonium fluoborate was stirred at room temperature for 4½ hours. The mixture was concentrated to dryness, and the residue was treated with 50 ml. of concentrated ammonium hydroxide, and sodium hydroxide solution. The strongly basic mixture was extracted 5 times withchloroform. The chloroform extract was extracted with dilute hydrochloric acid. The acid extract was made basic with sodium hydroxide solution and extracted 5 times with chloroform. The chloroform extract was washed with water, dried (Na$_2$SO$_4$) and concentrated to dryness to give 1.89 of oily 2-imino-1-methyl-1,2,5,6-tetrahydropyridine. Conversion to the oxalate salt and recrystallization from ethanol/ether gave 1.23 g. of 2-imino-1-methyl-1,2,5,6-tetrahydropyridine, hydrogen oxalate, m.p. 110°–112° C.

EXAMPLE 3

6-Amino-2-imino-1-methyl-1,2-dihydropyridine

Step A: Preparation of methyl 2,6-difluoropyridinium fluorosulfonate

A mixture of 5 g. of 2,6-difluoropyridine and 15 g. of methyl fluorosulfonate was warmed at 70°–100° C. for 4 minutes. The solid mass was cooled, suspended in methylene chloride and collected on a filter to give 9.9 g. of methyl 2,6-difluoropyridinium fluorosulfonate.

Step B: Preparation of 6-amino-2-imino-1-methyl-1,2-dihydropyridine

Methyl 2,6-difluoropyridinium fluorosulfonate (2 g.) was added to excess concentrated ammonium hydroxide solution, and the mixture was evaporated to dryness. The residue was stirred in acetonitrile and filtered. The filtrate was concentrated to dryness. The residue was suspended in chloroform and collected on a filter to give 1.08 g. of 6-amino-2-imino-1-methyl-1,2-dihydropyridine, fluorosulfonate. This material was dissolved in 50 ml. of ethanol and treated with 6 g. of solid potassium carbonate, stirred for 3 hours, and concentrated to dryness. The residue was stirred in isopropanol and filtered. The filtrate was treated with 1 g. of oxalic acid in isopropanol. The precipitate was collected, dissolved in hot ethanol, treated with decolorizing charcoal, for 5 minutes, filtered and concentrated to dryness. The residue was suspended in isopropanol and collected on a filter to give 950 mg. of 6-amino-2-imino-1-methyl-1,2-dihydropyridine, hydrogen oxalate, which after recrystallization from ethanol, had m.p. 166°–168° C. (dec.).

EXAMPLE 4

Pharmaceutical Compositions

A typical tablet containing 150 mg. of 2-imino-1-methylpyrrolidine per tablet is prepared by mixing together with the active ingredient calcium phosphate, lactose and starch in the amounts shown in the table below. After these ingredients are thoroughly mixed, the dry mixture is blended for an additional three minutes. This mixture is then compressed into tablets. Similarly prepared are tablets containing 2-imino-1-methyl-1,2,5,6-tetrahydropyridine or other compound within the scope of this invention.

| Tablet Formula | |
| --- | --- |
| Ingredient | Mg. per tablet |
| Active Ingredient | 150 mg. |
| Calcium phosphate | 52 mg. |
| Lactose | 60 mg. |
| Starch | 10 mg. |
| Magnesium stearate | 1 mg. |

What is claimed is:

1. A method of inhibiting indoleamine-N-methyltransferase which comprises administering to a patient in need of such treatment an effective enzyme-inhibiting amount of a compound of formula:

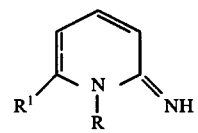

or a pharmaceutically acceptable salt thereof, wherein
R is lower alkyl,
$R^1$ is hydrogen or amino, and the broken line represents saturation or unsaturation.

2. A pharmaceutical composition which inhibits indoleamine-N-methyltransferase in unit dosage form comprising a pharmaceutical carrier and an effective enzyme-inhibiting amount of a compound of formula:

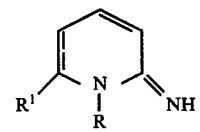

or a pharmaceutically acceptable salt thereof, wherein
R is lower alkyl,
$R^1$ is hydrogen or amino, and the broken line represents saturation or unsaturation.

3. The composition of claim 2 wherein the compound has the structure:

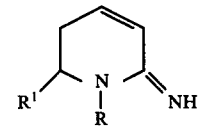

or a pharmaceutically acceptable salt thereof.

4. The compound, 2-imino-1-methyl-1,2,5,6-tetrahydropyridine.